United States Patent
Anderson et al.

(10) Patent No.: US 9,138,246 B2
(45) Date of Patent: Sep. 22, 2015

(54) ELBOW RECONSTRUCTION INSTRUMENTS AND TECHNIQUES

(75) Inventors: Kyle Anderson, Birmingham, MI (US);
Neal S. ElAttrache, Los Angeles, CA (US); William C. Benavitz, Naples, FL (US); John E. Conway, Fort Worth, TX (US); Anthony A. Romeo, Burr Ridge, IL (US); Derek C. Sullivan, Bonita Springs, FL (US); Jonathan H. Webb, Midland, TX (US)

(73) Assignee: Arthrex, Inc., Naples, FL (US)

( * ) Notice: Subject to any disclaimer, the term of this patent is extended or adjusted under 35 U.S.C. 154(b) by 752 days.

(21) Appl. No.: 13/028,690

(22) Filed: Feb. 16, 2011

(65) Prior Publication Data
US 2011/0208198 A1    Aug. 25, 2011

Related U.S. Application Data

(60) Provisional application No. 61/306,346, filed on Feb. 19, 2010.

(51) Int. Cl.
*A61B 17/56* (2006.01)
*A61B 17/17* (2006.01)
*A61B 17/88* (2006.01)
*A61F 2/08* (2006.01)

(52) U.S. Cl.
CPC ......... *A61B 17/1739* (2013.01); *A61B 17/1796* (2013.01); *A61B 17/8861* (2013.01); *A61F 2/0811* (2013.01)

(58) Field of Classification Search
CPC ............... A61B 17/17; A61B 17/1714; A61B 17/1717; A61B 17/1728; A61B 17/1739; A61B 2017/1782
USPC ........ 606/86 R, 87, 80, 300–301, 321, 96–98
See application file for complete search history.

(56) References Cited

U.S. PATENT DOCUMENTS

| | | | | |
|---|---|---|---|---|
| 6,120,511 | A | * | 9/2000 | Chan ............................... 606/96 |
| 2004/0092947 | A1 | * | 5/2004 | Foley .............................. 606/96 |
| 2009/0018654 | A1 | * | 1/2009 | Schmieding et al. ...... 623/13.14 |
| 2009/0228017 | A1 | * | 9/2009 | Collins ........................... 606/96 |

* cited by examiner

*Primary Examiner* — Anu Ramana
*Assistant Examiner* — Jessica Weiss
(74) *Attorney, Agent, or Firm* — Dickstein Shapiro LLP (57) ABSTRACT

Techniques and instrumentation for elbow reconstruction, specifically, for repairs of the ulnar collateral ligament (UCL). The instrumentation provides for precise formation of sockets and tunnels along with easy suture/graft passage while accommodating all forms of elbow UCL reconstruction techniques. A V-drill guide is provided with a handle and two drill sleeves having intersecting trajectories for creating an intersecting V-shaped bone tunnel in the ulna. An adjustable humeral guide has an adjustable arm with an arc shape, and a peg and a block extending from each end of the adjustable arm. The peg is shaped to fit within an already-formed humeral socket. The block allows a drill to pass through and form other tunnels which intersect with the originally-formed tunnel at various positions.

4 Claims, 10 Drawing Sheets

FIG. 12

ELBOW RECONSTRUCTION INSTRUMENTS AND TECHNIQUES

CROSS-REFERENCE TO RELATED APPLICATIONS

This application claims the benefit of U.S. Provisional Application No. 61/306,346, filed Feb. 19, 2010, the entire disclosure of which is incorporated by reference herein.

FIELD OF THE INVENTION

The present invention relates to surgical instruments and technique to reconstruct the elbow, in particular, the ulnar collateral ligament (UCL).

BACKGROUND OF THE INVENTION

When soft tissue such as a ligament or a tendon becomes detached from a bone, surgery is usually required to reattach or reconstruct the tissue. When the ligament is the ulnar collateral ligament (UCL) of the medial elbow, a graft may be used to replace the entire ligament to facilitate regrowth and permanent attachment. Instrumentation and techniques to facilitate this repair are needed.

SUMMARY OF THE INVENTION

The present invention provides new and improved instrumentation for elbow reconstruction, specifically, for repairs of the ulnar collateral ligament (UCL). The instrumentation of the present invention provides for precise formation of sockets and tunnels along with easy suture/graft passage while accommodating all forms of elbow UCL reconstruction techniques.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

The present invention provides surgical systems and methods for repair of soft tissue, specifically, for reattaching or replacing the ulnar collateral ligament to the humerus and ulna. The systems of the present invention contain various instruments such as drills, guides, obturators, suturelassos and skids that allow precision formation of sockets and tunnels along with easy suture/graft passage, while accommodating all forms of elbow UCL reconstruction.

A method for attaching the graft includes, for example, the steps of creating a bone tunnel in the humerus, creating a bone tunnel in the ulna, placing the graft through the tunnels, and attaching at least one end of the graft to the humeral bone.

Referring now to the drawings, where like elements are designated by like reference numerals, FIGS. 1-12 illustrate exemplary instruments and methods for creating elbow tunnels and passing graft through tunnels.

Figure 1:
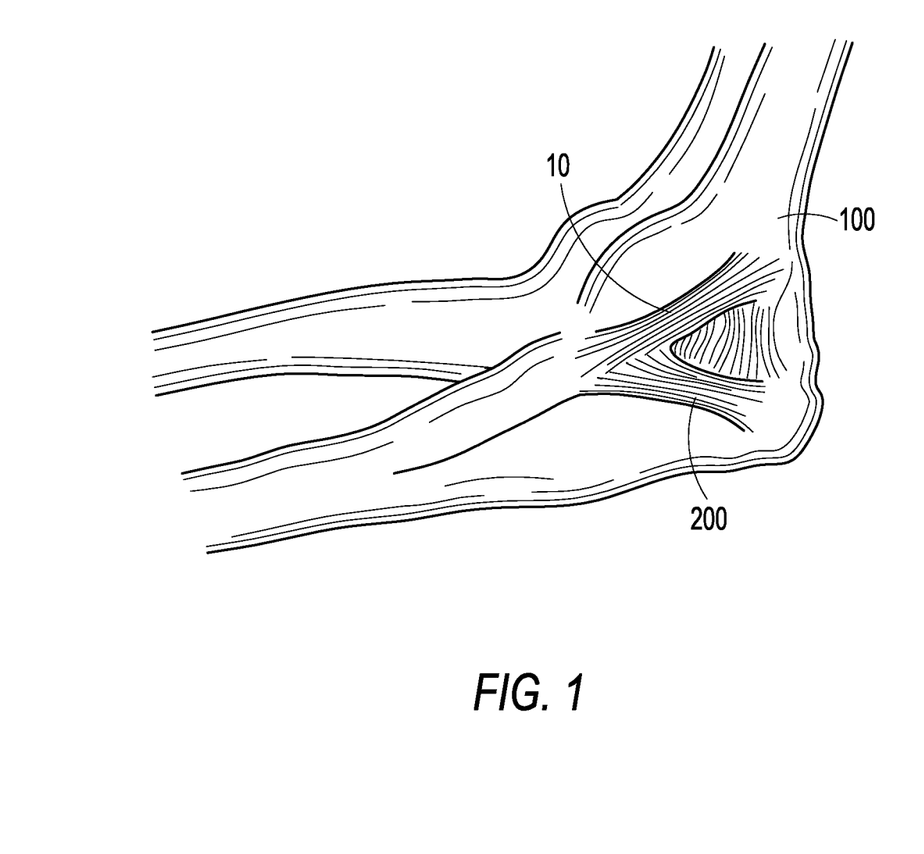
FIG. 1 illustrates the location of the ulnar collateral ligament between the ulna and humerus.

FIG. 1 illustrates ulnar collateral ligament 10 attached to the humeral bone 100 on one end and to the ulna bone 200 on the other end. In an exemplary method of replacing the UCL, a graft is secured within tunnels formed in the humerus 100 and the ulna 200. In one embodiment, a bone tunnel 380 is formed on the ulna 200 using a V-drill guide 300.

Figure 2:
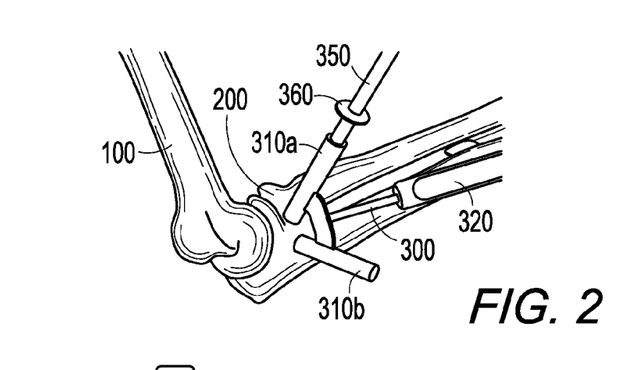
FIG. 2 illustrates a V-drill guide instrument of the present invention in position on the ulna (for drilling along with a drill used to drill a bone tunnel).

FIG. 2 illustrates the V-drill guide 300 of the present invention positioned on the ulna 200. Also shown in FIG. 2 is a drill bit 350 which is inserted through one of the sleeves of the V-drill guide 300 for drilling a bone tunnel in the ulna, as detailed below.

Figure 2A:
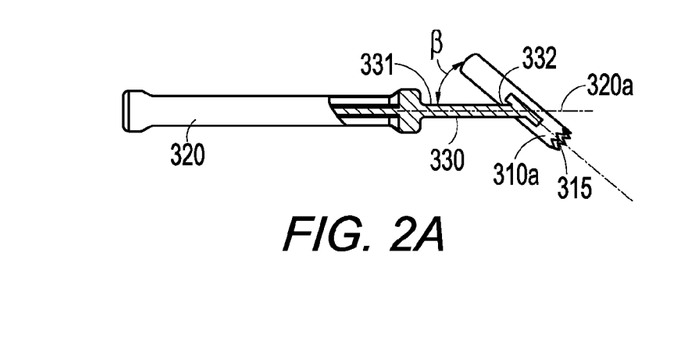
FIG. 2A illustrates a cross-sectional view of the V-drill guide instrument of the present invention.
Figure 2B:
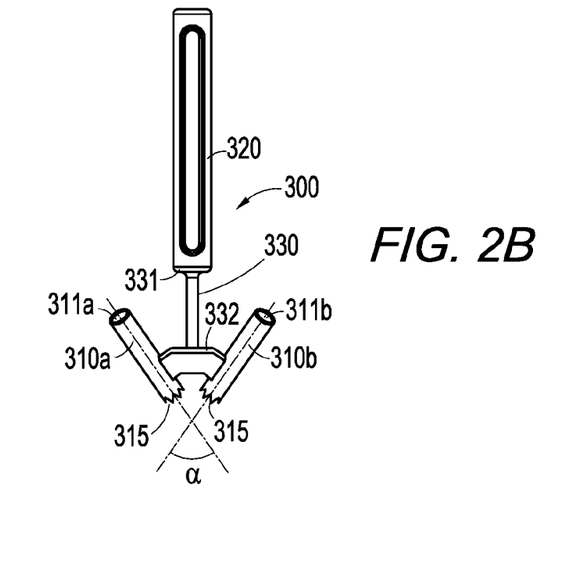
FIG. 2B illustrates a front view of the V-drill guide instrument of the present invention.
Figure 2C:
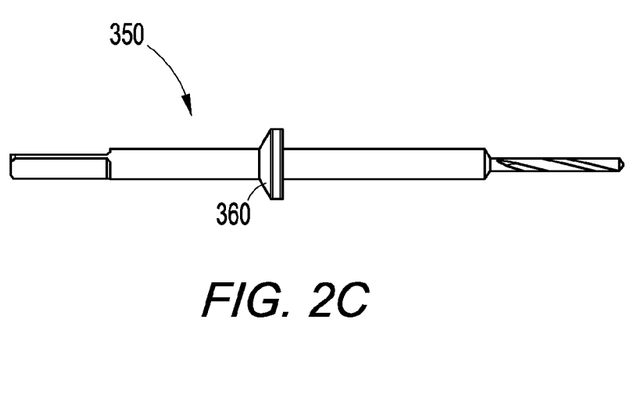
FIG. 2C illustrates a front view of the drill of FIG. 2 used with the V-drill guide instrument of the present invention.
Figure 3:
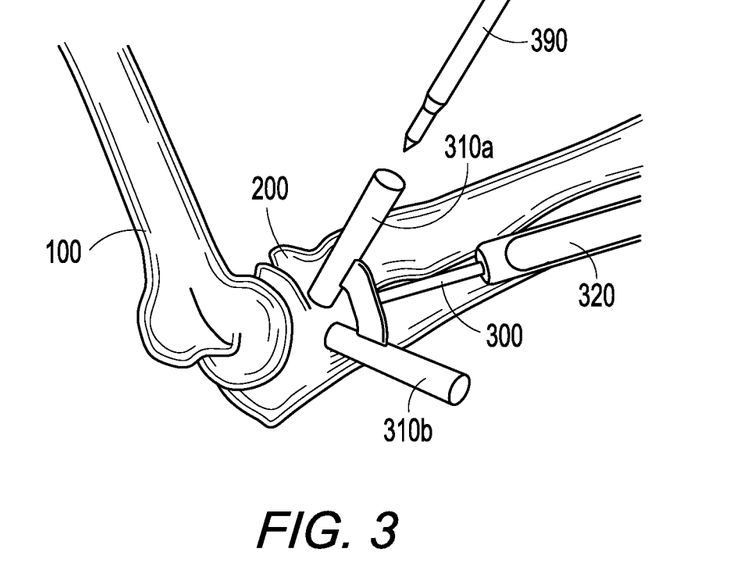
FIG. 3 illustrates the V-drill guide of FIGS. 2A-B in position with an obturator inserted through the guide.
Figure 3A:
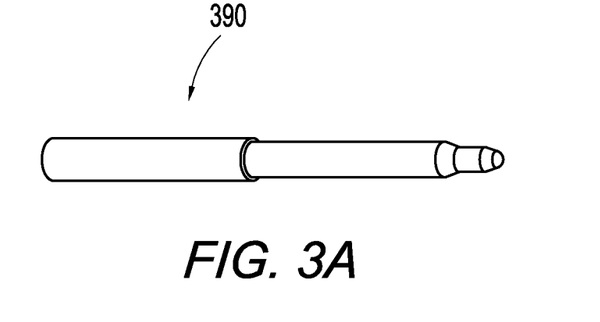
FIG. 3A illustrates a perspective view of the obturator of FIG. 3.

As shown in FIGS. 2A and 2B, V-drill guide 300 is provided with an elongated substantially rigid member 330 with a longitudinal axis 320a, a proximal end 331 and a distal end 332. A handle 320 is located at the proximal end 331 of the elongated member 330. Two drill sleeves 310a, 310b having intersecting trajectories for creating an intersecting bone tunnel (a V-shaped bone tunnel) are provided at the distal end 332 of the elongated member 330. The V-drill guide may have any number of trajectories but, in the preferred embodiment, angle a (FIG. 2B) is between 50 and 75 degrees. Distal end of drill sleeve 310a, 310b may have teeth 315 (FIGS. 2A and 2B) for gripping bone.

As also shown in FIG. 2A, each drill sleeve 310a, 310b extends in a direction non-parallel to the longitudinal axis 320a of the handle 320 and the elongated member 330, forming an angle β with the longitudinal axis 320a. Angle β is preferably between 30 to 45 degrees, more preferably about 45 degrees. Each drill sleeve 310a, 310b is provided with a lumen 311a, 311b that is sized and configured to receive a surgical instrument such as a drill, a pin or an obturator, for example.

Drill bit 350 (illustrated in FIGS. 2 and 2C) is used to drill through the drill sleeve 310a of the V-drill guide 300. Drill bit 350 may have a stop 360 (FIG. 2C) to limit the depth drilled.

Figure 4:
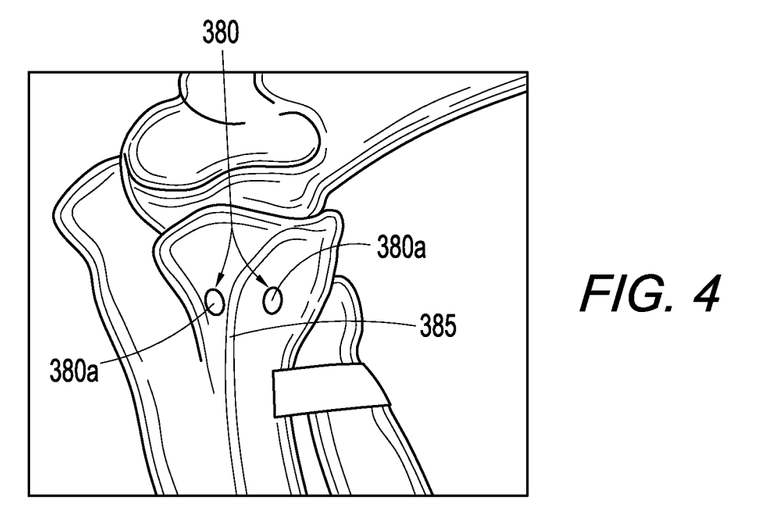
FIG. 4 illustrates the tunnel created using the V-drill guide of FIGS. 2A-B.

An obturator 390 (shown in FIGS. 3 and 3A) may be placed in drill sleeve 310a to hold the drill guide 300 in position while drill bit 350 drills through the second drill sleeve 310b. Once drilling is completed, a tunnel 380 approximately 1-2 cm distal from the articulating surface of the ulna, anterior and posterior to the sublime tubercle of the ulna, is created. As illustrated in FIG. 4, a bone bridge 385 is also created between openings 380a of the tunnel 380 (i.e., the length of bone extending between the centers of the two openings 380a). The V-drill guide 300 (depending on the angle) can create a bone bridge of between about 5.5 mm and 7.5 mm. This bone bridge avoids any possible fracture of the tunnel into the ulnohumeral joint.

Once bone tunnel 380 has been created, a skid 500 (FIG. 5) is fully inserted into the tunnel 380. A suture/wire passing instrument 600 (for example, a retrograde suture passing instrument such as a suturelasso) (FIG. 5) is inserted from the opposite end of the tunnel and the wire loop 650 (FIG. 6) is advanced until it reaches the skid within the tunnel. The skid 500 provides a smooth path for the wire loop to follow through the tunnel.

Figure 5:
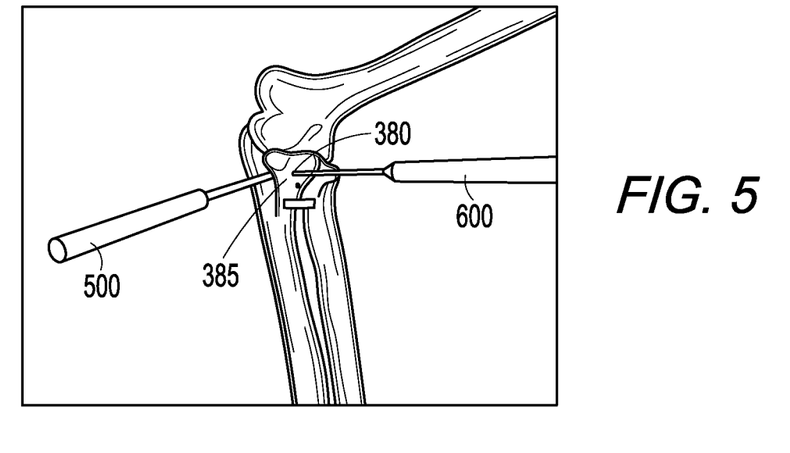
FIG. 5 illustrates the skid instrument and the suturelasso inserted into the tunnel shown in FIG. 4.
Figure 6:
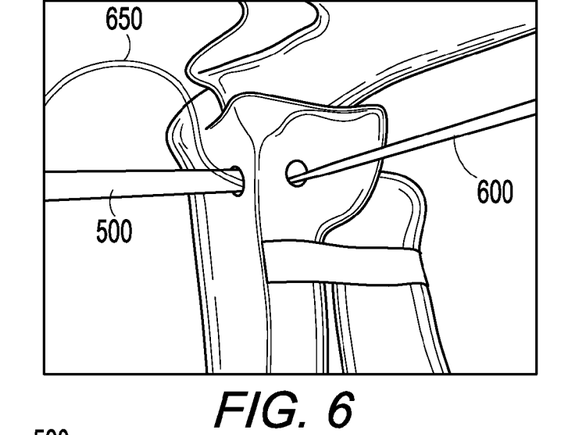
FIG. 6 illustrates the wire loop of the suturelasso of FIG. 5, exiting from the other end of the tunnel through the skid.
Figure 6A:
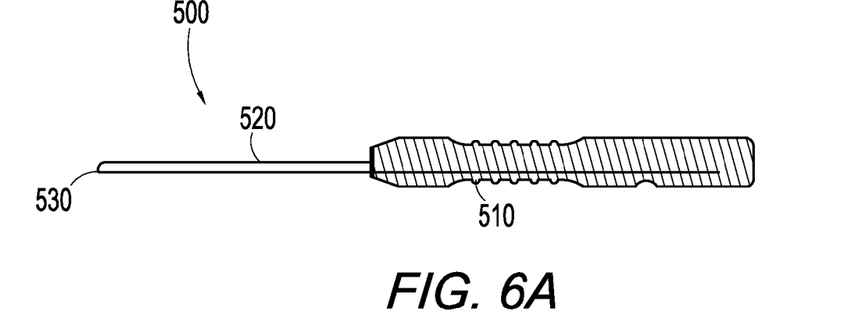
FIGS. 6A-C illustrate various views (a cross-sectional view, a top view, and a left side view, respectively) of the wire skid shown in FIGS. 5 and 6.
Figure 6B:
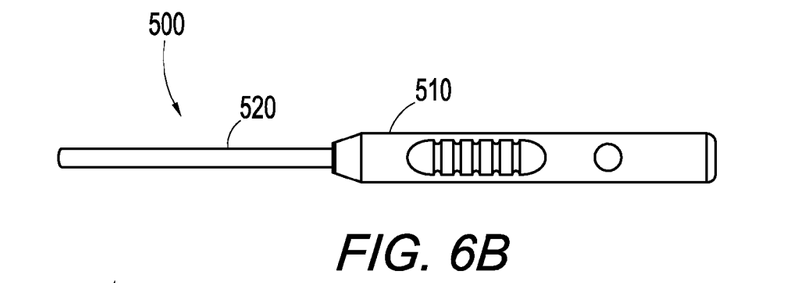
Figure 6C:
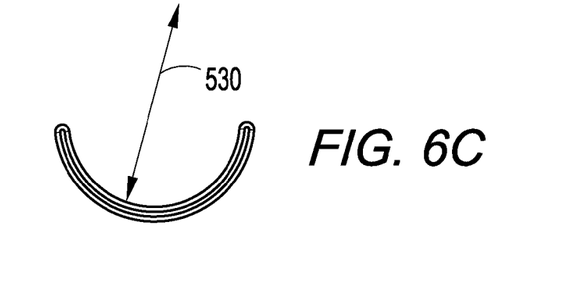

As shown in FIGS. 6A and 6B, skid 500 has a handle 510 and a shaft 520. The shaft 520 has a u-shape channel 530 (FIG. 6C) for the wire loop to contact and create a smooth passageway through the tunnel. The position of the wire loop 650 outside the bone tunnel 380 facilitates passing sutures and the graft in the tunnel. FIGS. 5-6C illustrate the skid 500 and suturelasso 600 passing through the tunnel 380.

In an alternate embodiment, instead of creating an intersecting bone tunnel in the ulna (such as the formation of intersecting V-shaped bone tunnel 380 detailed above), a through tunnel may be created using an offset guide 700.

Figure 7:
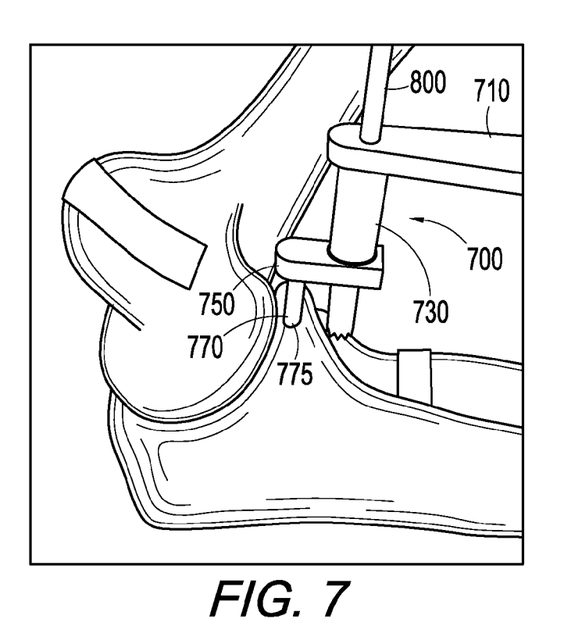
FIG. 7 illustrates an offset guide of the present invention (an optional instrument) for creating a tunnel in the ulna, and in position on the ulna.
Figure 7A:
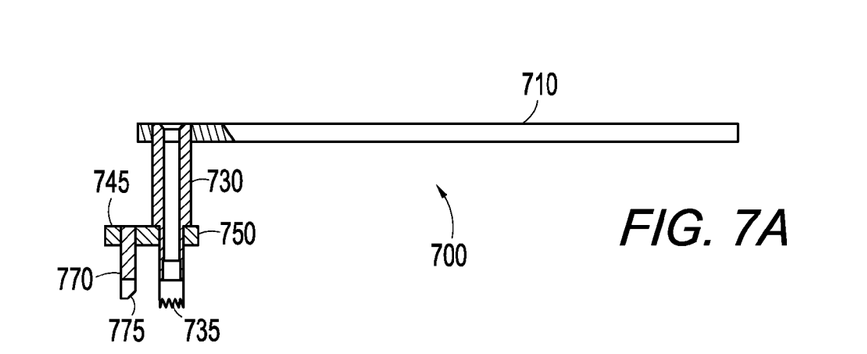
FIGS. 7A and B illustrate a cross-sectional view and a perspective view, respectively, of the offset guide of FIG. 7.
Figure 7B:
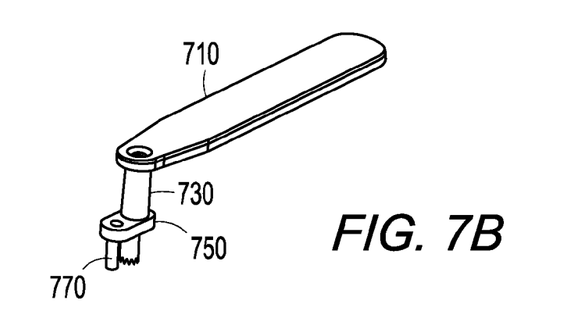

Offset guide 700 is shown in FIGS. 7-7B with handle 710. A cannulated tube 730 extends from handle 700 and through platform 750. Cannulated tube 730 may have teeth 735 (FIG. 7A) at its most distal end to provide better gripping of the bony surface. Platform 750 (FIG. 7B) is generally rectangular in shape with a bore 745 for tube 730 to pass through and a prong 770 for placing against bone for stability. Prong 770 has a generally cylindrical shape with a distal flat side 775 contoured to approximate the bony anatomy of the ulna. The prong 770 is placed at the sublime tubercle of the ulna. The platform 750 extends away from the prong placing the cannulated tube 730 a set distance from the sublime tubercle in the desired spot for drilling the tunnel through the cannulated tube.

A pin 800 (FIG. 7) is placed through the cannulated tube 730 of the offset guide 700 and drilled through the bone. A reamer 900 is placed over the pin 800 and used to ream out a partial length of the tunnel to accommodate an end of the graft. A button could be used to attach the graft to the ulna. Alternately, if a screw is to be used for fixing the graft, the reamer would be used to ream the entire tunnel.

Figure 8:
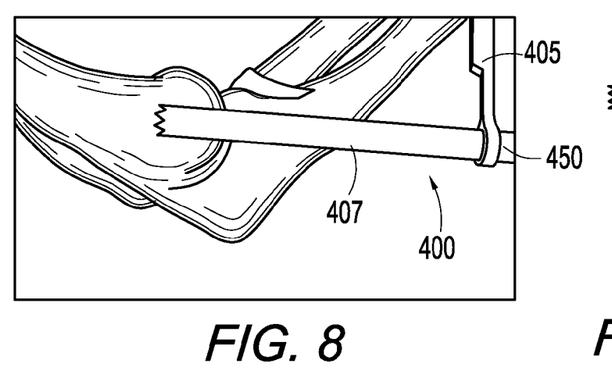
FIG. 8 illustrates a humeral drill guide of the present invention for creating a tunnel in the humerus, and in position on the humerus.
Figure 8A:
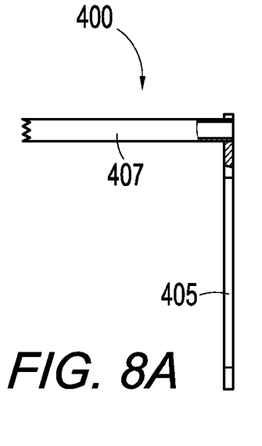
FIG. 8A illustrates a partial cross-sectional view of the humeral drill guide of FIG. 8.
Figure 8B:
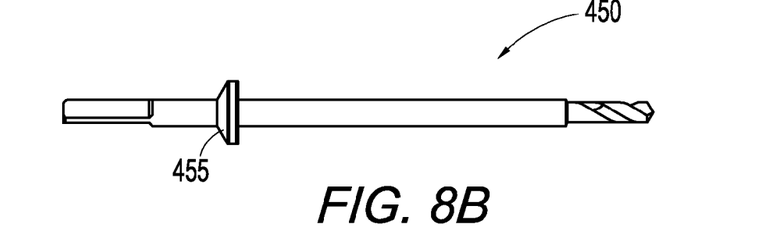
FIG. 8B illustrates a front view of a drill used with the humeral drill guide of FIG. 8.

To complete the UCL reconstruction surgery, a second bone tunnel is formed in the humerus bone 100. Humeral socket drill guide 400 (FIGS. 8 and 8A) is used to drill an approximately 15 mm deep socket in the humerus with drill bit 450. As shown in FIGS. 8 and 8A, humeral socket drill guide 400 includes a handle 405 with a cannulated tube 407 extending from the handle. A drill 450 (shown in FIG. 8B) with a depth stop 455 is placed through the cannulated tube 407 of the humeral socket drill guide 400 to create a socket 410 in humerus 100.

Figure 9:
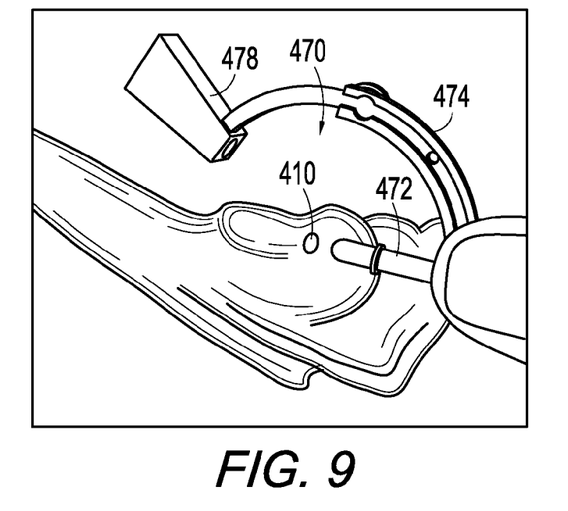
FIG. 9 illustrates an adjustable drill guide of the present invention, for creating an intersecting tunnel in the humerus, and in position on the humerus.
Figures 9A, 9B, 9C:
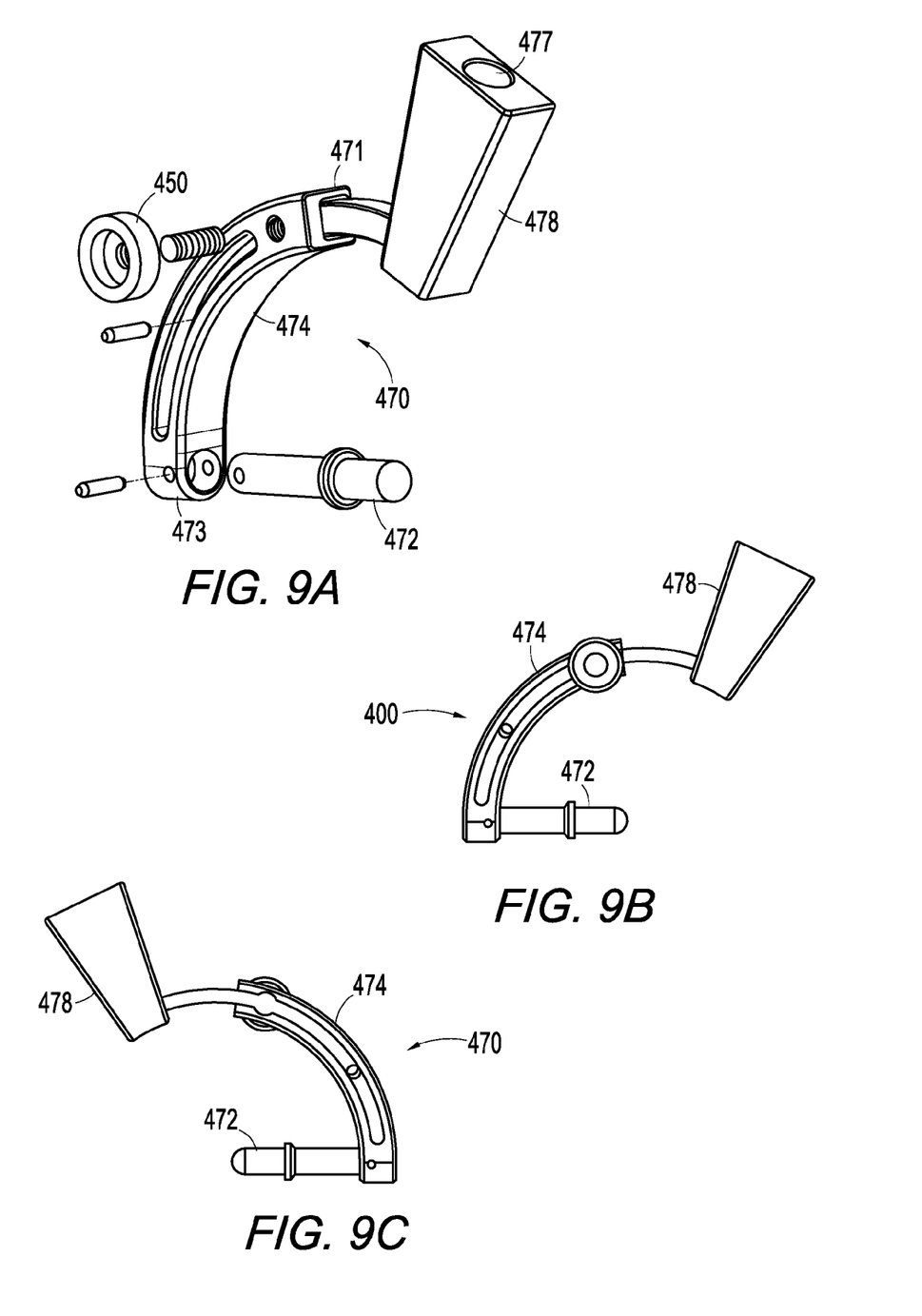
FIG. 9A illustrates an exploded perspective view of the adjustable drill guide of FIG. 9.
FIG. 9B illustrates a front view of the adjustable drill guide of FIG. 9A.
FIG. 9C illustrates a back view of the adjustable drill guide of FIG. 9A.
Figure 10:
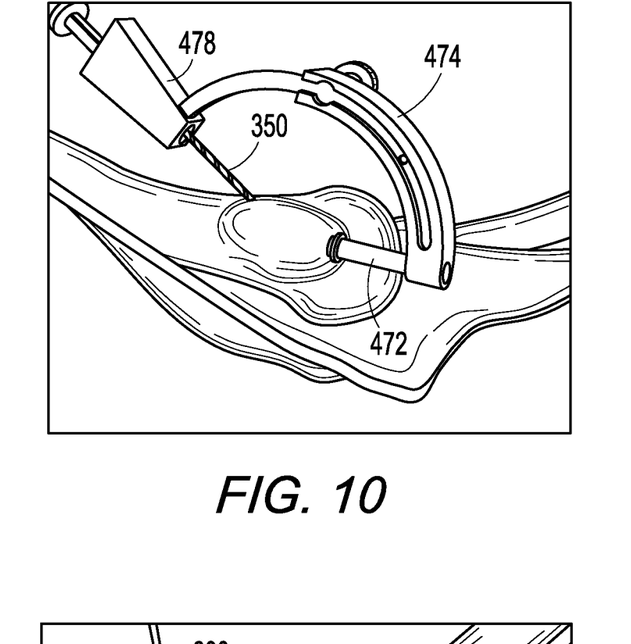
FIG. 10 illustrates the adjustable drill guide of FIG. 9, in position on the humerus, and with a drill extending through the guide portion.

Adjustable humeral guide 470 is designed to fit into the socket 410 as shown in FIG. 9. Various views of the adjustable humeral guide 470 are illustrated in FIGS. 9A-C. Adjustable humeral guide 470 has an adjustable arm 474 with a proximal end 471 and a distal end 473 having an arc shape. A peg 472 extends from the distal end 473 of the adjustable arm 474. Peg 472 is shaped to fit within the socket 410 created using the humeral drill guide 400. Block 478 extends from the proximal end 471 of the adjustable arm and has a passageway 477 extending through, and sized for a drill to pass through. Adjustable humeral guide 470 allows for at least one hole 411 to be drilled which intersects with the original socket 410 at various positions. The guide may pivot and slide covering various angles in reference to the peg 472 situated within the original socket 410 which allows the surgeon to choose the best position for situating the graft. The block 478 slides on the adjustable arm 474 and may be securely fixed relative to the peg 472 by a securing device 450, such as a knob for example (FIG. 9A). The same drill 350 used to create the intersecting tunnel in the ulna is used with the adjustable humeral guide 470 to create an intersecting tunnel 411 in the humerus, as illustrated in FIG. 10.

Figure 11:
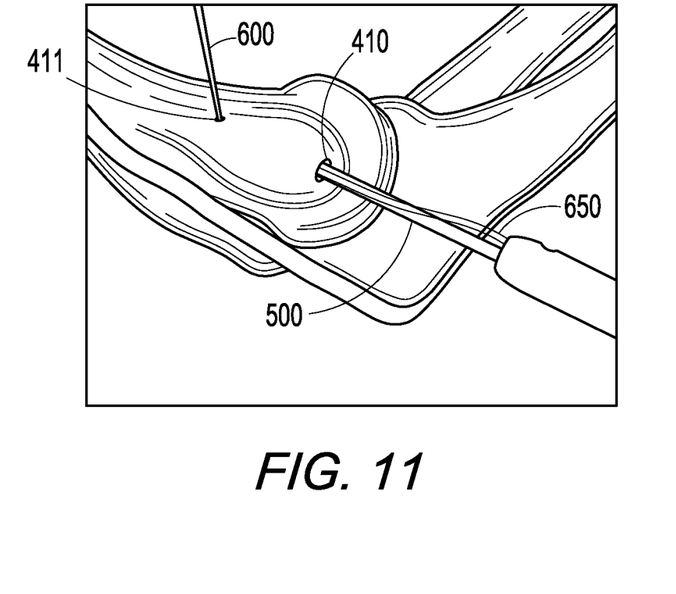
FIG. 11 illustrates a suturelasso and skid extending through the humeral tunnel created by the adjustable drill guide of FIG. 9.

Skid 500 is used with the wire loop 650 of suturelasso 600 in a similar manner as in the ulna, to pass sutures and the graft through the tunnel as illustrated in FIG. 11.

Figure 12:
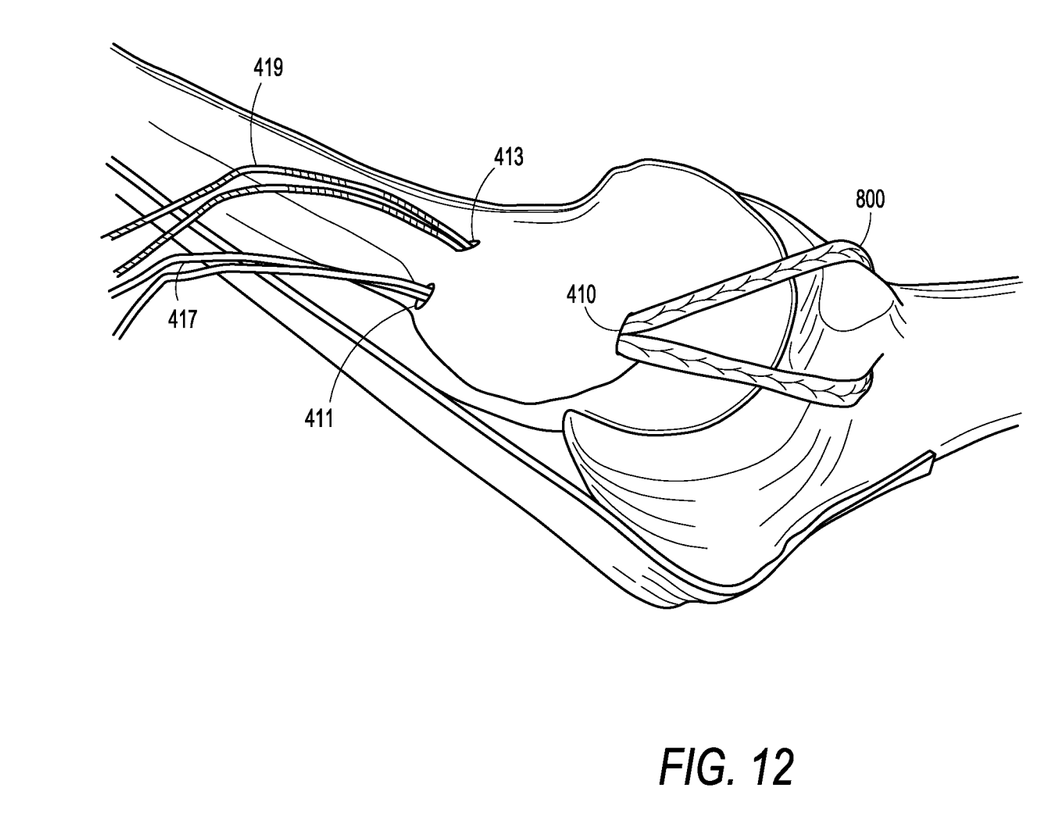
FIG. 12 illustrates the formation of two intersecting tunnels in the humerus, and according to an exemplary embodiment of the present invention.

FIG. 12 illustrates another embodiment of the present invention according to which at least two intersecting tunnels are formed in the humerus, each formed with the adjustable humeral guide 470 of the present invention. The design of the adjustable humeral guide 470 allows for a plurality of holes/tunnels to be drilled, each of the plurality of the holes/tunnels intersecting with the original socket 410 at various positions and angles.

FIG. 12 illustrates an exemplary embodiment only, according to which a third humeral tunnel 413 is also drilled using the adjustable humeral guide 470, in addition to the second humeral tunnel 411. The result is having two holes/tunnels 411, 413 at different trajectories that both intersect with the original tunnel 410. If desired, and depending on the patient's anatomy, more than three tunnels (i.e., more than two intersecting tunnels) can be formed. FIG. 12 shows a simulation of graft 800 being pulled through the first tunnel 410, with the attached sutures 417, 419 being pulled through the second and third intersecting humeral tunnels 411, 413. These sutures 417, 419 can be tied together across the bone bridge or a button could be used to knot them individually.

Once the tunnels are created in both the ulna and the humerus, various known methods such as the Tommy Jones method, the modified Tommy Jones method, the Docking method, the Interference Screw method, or the Hybrid-Interference Screw method may be used to place and attach the graft.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of ulnar collateral ligament reconstruction, comprising the steps of:
    forming an intersecting V-shaped bone tunnel in the ulna by placing a V-drill guide over the sublime tubercle of the ulna, the V-drill guide comprising a handle having a longitudinal axis, a proximal end and a distal end; and two drill sleeves located at the distal end of the handle, wherein the drill sleeves are symmetrically disposed relative to the longitudinal axis of the handle and a mirror image of each other and having intersecting trajectories, the drill sleeves being non-parallel relative to each other and forming an angle of 50 to 75 degrees between them, the drill sleeves being non-parallel to the longitudinal axis of the handle, wherein a distal end of each of the drill sleeves is provided with teeth for gripping bone, and drilling a tunnel through each of the drill sleeves with a drill sized to pass through each of the two drill sleeves so that a resulting intersecting V-shaped tunnel is achieved and so that openings of the resulting intersecting V-shaped bone tunnel define a bone bridge on the ulnar cortex, the bone bridge having a length between the openings of 5.5 mm to 7.5 mm;
    forming at least one intersecting humeral tunnel in the humerus by placing an adjustable humeral guide over the humerus, the adjustable humeral guide comprising an adjustable arm, and a peg and a block extending from the adjustable arm, the block being provided with a bore to allow the drill to pass therethrough and to form the at least one intersecting tunnel within the humerus, wherein the drill is sized to pass through both the two drill sleeves of the V-drill guide and through the bore of the block of the adjustable humeral guide; and
    securing a graft in the intersecting V-shaped bone tunnel and the humeral tunnel.

2. The method of claim 1, wherein the at least one intersecting humeral tunnel is formed by:
    forming a first socket or tunnel through the humerus;
    placing the adjustable humeral guide over the humerus, the adjustable humeral guide comprising the adjustable arm having a proximal end and a distal end, and an arc-shaped configuration; the peg extending from the distal end of the adjustable arm, the peg being configured and sized to fit within the first socket tunnel; and the block extending from the proximal end of the adjustable arm, the block being provided with the bore to allow the drill to pass therethrough and to form at least one second socket or tunnel within the humerus, the at least one second socket or tunnel intersecting the first humeral tunnel at different angles;
    fitting the peg of the adjustable humeral guide within the first socket or tunnel;
    adjusting the block relative to the peg and securely positioning the block relative to the peg; and
    inserting the drill through the bore of the block and drilling to form at least one second socket or tunnel, the at least one second socket or tunnel intersecting the first humeral tunnel at an angle.

3. The method of claim 2, further comprising the step of forming two second sockets or tunnels intersecting the first humeral tunnel at different angles.

4. The method of claim 1, wherein the step of securing the graft in the intersecting V-shaped bone tunnel and the humeral tunnel is conducted by employing at least one of an interference screw, a button, or a suture/loop button construct comprising a continuous, uninterrupted loop of suture attached to a button.

* * * * *